United States Patent [19]

Moret

[11] 4,266,535
[45] May 12, 1981

[54] DIAGNOSTIC LAMP

[75] Inventor: Michel A. Moret, Chene-Bourg, Switzerland

[73] Assignee: Les Produits Associes BPA SA, Chene-Bourg, Switzerland

[21] Appl. No.: 29,541

[22] Filed: Apr. 12, 1979

[30] Foreign Application Priority Data

Apr. 14, 1978 [CH] Switzerland ............ 4020/78

[51] Int. Cl.³ .................. A61B 1/24; A61B 1/06
[52] U.S. Cl. ...................... 128/23; 433/29; 362/804; 350/1.6
[58] Field of Search .......... 128/22, 23, 11, 13, 128/16, 18, 395, 396, 362; 362/804; 433/29; 350/1.4, 1.6

[56] References Cited

U.S. PATENT DOCUMENTS

| | | | |
|---|---|---|---|
| 3,704,928 | 12/1972 | Coombs et al. | 362/804 X |
| 3,711,700 | 1/1973 | Westlund, Jr. et al. | 128/23 X |
| 4,184,196 | 1/1980 | Moret et al. | 362/804 |
| 4,195,329 | 3/1980 | Woog | 362/155 |

FOREIGN PATENT DOCUMENTS

| | | | |
|---|---|---|---|
| 2725793 | 1/1978 | Fed. Rep. of Germany | 128/23 |
| 7530608 | 6/1977 | France | 128/23 |

*Primary Examiner*—Kyle L. Howell
*Attorney, Agent, or Firm*—Kane, Dalsimer, Kane, Sullivan and Kurucz

[57] ABSTRACT

A portable diagnostic lamp is constructed as a pocket appliance for inspecting teeth by fluorescent excitation of a fluorescible material which has been applied to the teeth and gums. A lamp comprises a casing housing a small battery-powered incandescent bulb with a lens supplying a divergent beam of rays and a rectangular filter located before the latter, which filter comprises a blue color filter with a dichroic filter applied thereto. A folding and adjustable mirror is located above the bulb, in use of the lamp and the longer sides of the rectangular filter and a filament of the incandescent bulb are arranged parallel to the pivot axis of the mirror.

9 Claims, 4 Drawing Figures

DIAGNOSTIC LAMP

BACKGROUND OF THE INVENTION

The invention relates to a diagnostic lamp for fluorescent excitation of a fluorescible material applied to the teeth.

It is known to make plaque which is not normally visible, i.e. the deposits on the teeth consisting mainly of bacteria and causing diseases of the teeth and gums, easily recognizable by painting a fluorescible material on the teeth so that fluorescent radiation can then be stimulated by means of a suitable lamp. It has been shown that fluorescible materials adhere solely or at least preferably to the plaque, but not to the clean and healthy areas of the teeth and gums. The same is true for those places where tartar has formed due to mineralisation of the plaque or which have already fallen prey to caries. Therefore, these critical or unhealthy parts of the teeth can be made visible and localised in a simple manner by the afore-described inspection, since when illuminated, only these areas flouresce and thus stand out from the other non-fluorescent areas.

A diagnostic lamp for inspecting the teeth, which is constructed in the form of a pocket appliance and is provided with an exchangeable dispenser for a fluorescible material is already known from U.S. Pat. No. 4,195,329 by the same applicant. The following difficulties occurred in the search for improvements to the degree of optical efficiency of this diagnostic lamp, which is preferably operated with the lowest possible power, and in the search for ways of increasing the visible contrast between fluorescent areas and non-fluorescent areas which are solely reflecting areas:

A fluorescible material which is best suited in practice is a fluorescein solution. The spectrum for the stimulation of a typical fluorescein solution with visible light comprises the wave length range of between approximately 450 and 410 nm, i.e. substantially blue light, the absorption maximum in a typical case being 495 nm. The maximum fluorescent radiation emitted is at only slightly higher wave lengths, namely at approximately 525 nm. In order that this fluorescence spectral range and as far as possible the remaining visible light of longer wave lengths are blocked out in a satisfactory manner from the light of the incandescent bulb, a dichroic filter of corresponding dimensions is most suitable, whose transmission curve falls steeply at approximately 500 nm and, for perpendicularly incident light, only allows light to pass therethrough again in the long wave red or infrared range. However, in order that the light strikes the filter substantially at right-angles, one must have a beam of parallel rays, in which case the cross section of this beam of rays should be sufficiently large in order that at least approximately the entire set of teeth or the entire mouth cavity is illuminated upon inspection. However, a substantially larger lamp with a correspondingly more complicated optical arrangement would be necessary to fulfil this requirement.

However, if in order to avoid the use of a parallel beam of rays with a relatively large cross section, one were to use a divergent beam of rays, then, as was ascertained, a dichroic filter would allow all the more light to pass in the visible red range, the greater the angle of incidence of the radiation, i.e. the further the rays from the geometric axis of the beam. For rays striking the filter at an angle of 45°, the transmission curve of a dichroic filter once more increases steeply at approximately 650 nm. This has the result that when using a suitable divergent beam of rays, the illuminated area to be inspected appears red in the vicinity of the edge, in which case this reflected red light virtually covers any possible fluorescent radiation and makes the latter invisible, so that a reasonable inspection is impossible.

SUMMARY OF THE INVENTION

The object of the invention is to provide a diagnostic lamp of the afore-described type, which with a small incandescent bulb consuming little electrical power, for example a normal torch bulb and with very simple optical means, produces a beam of light which both illuminates a sufficiently large area for convenient inspection, with sufficient intensity as well as produces a good optical contrast between the fluorescent and non-fluorescent points within the entire illuminated area.

This provides the technical advantages that the radiation emitted by a small incandescent bulb is utilized in a virtually optimum manner and that despite a divergent beam of rays and the use of a dichroic filter, inspection of the teeth is not impaired or even compromised by coloring the edge regions red. Furthermore, the diagnostic lamp according to the invention has a further essential advantage in that the parts of the teeth not covered with the fluorescent substance and having a blueish reflection on account of the blue filter, contrast particularly well against the yellow or greenish yellow fluorescent radiation of the parts covered with the fluorescent substance.

In this respect it is worthy of note that in another known, substantially more complicated construction of inspection lamp for teeth, apart from a dichroic reflector behind the lamp and a dichroic filter in front of the lamp, a dichroic observation mirror is also provided, which has the same transmission and reflection properties as the filter and therefore allows the passage of the blue stimulating radiation, so that in the mirror, the illuminated teeth or areas of the teeth emitting no fluorescent radiation seem substantially yellow to the observer, since only the yellow is reflected by the dichroic mirror. However, due to this, the contrast with respect to the yellow or greenish yellow fluorescent radiation is greatly reduced or even eliminated, so that a reliable inspection is at least made difficult. As afore-mentioned, the diagnostic lamp according to the invention provides a substantially better contrast, which allows a particularly reliable inspection, whereby it is also possible to dispense with the expenditure for a separate dichroic mirror allowing partial transmission in favour of a completely normal mirror.

One embodiment of the invention is described in detail hereafter with reference to the drawings.

DETAILED DESCRIPTION OF THE INVENTION

Figure 1:
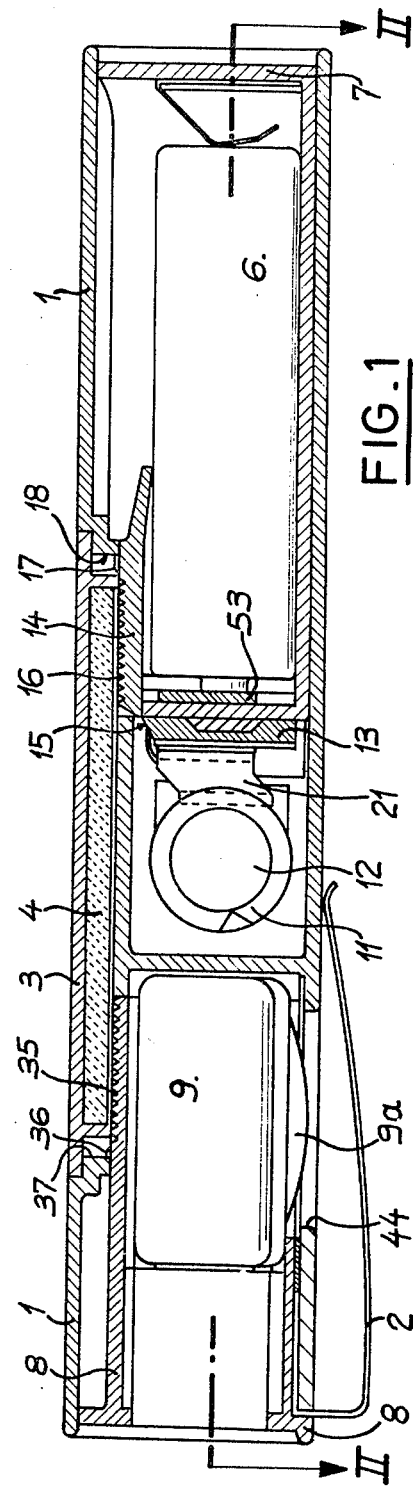
FIG. 1 is a longitudinal sectional view through the casing of the diagnostic lamp with a view towards one narrow side in the direction of arrow I according to FIG. 2, the lid with the mirror being closed.

The diagnostic lamp according to the drawings constructed as a pocket appliance has an elongated flat casing 1, whose narrow sides are rounded-off (FIG. 3) and which is selectively provided at one end with a securing clip 2 (FIG. 1). A lid 3 on whose inner side a concave mirror 4 is attached, is pivotally connected in the central region of the casing by means of a flexible part 5 consisting of synthetic material (FIG. 3), which is stuck to the inner surfaces of one longitudinal side of the casing and of the lid and serves as a hinge. Located in the casing 1 are an insert 7 supporting the batteries 6 together with the other electrical parts, which insert can be pushed into one end face of the casing and an insert 8 for the dispenser 9 containing a fluorescent solution, preferably fluorescein, which insert 8 can be pushed into the other end face of the casing.

Figure 2:
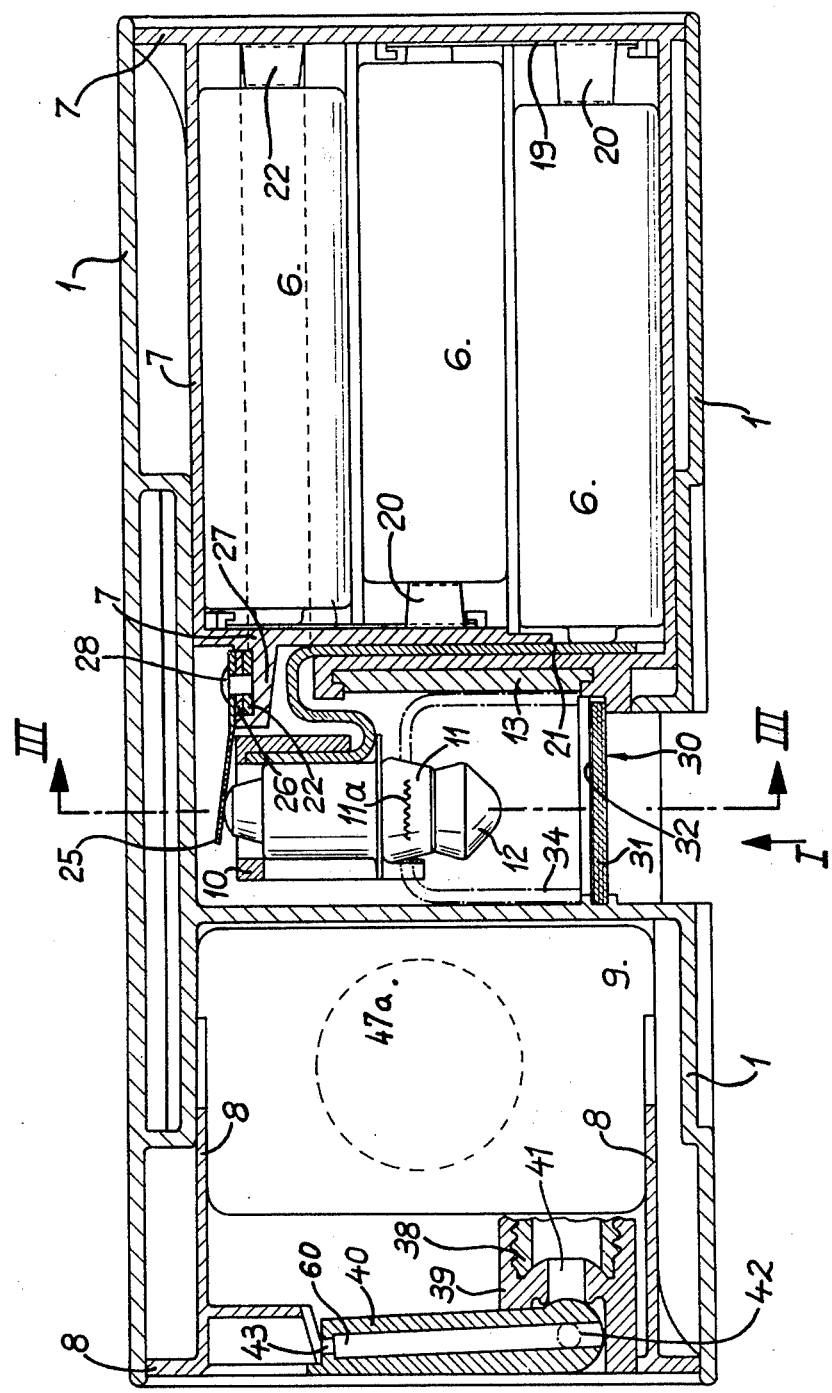
FIG. 2 is a longitudinal sectional view on line II—II according to FIG. 1 with a plan view of the batteries, incandescent bulb and dispenser.

Located approximately at the centre of the casing 1, below the lid 3 and between the two inserts 7 and 8 is a lamp holder 10 with a miniature incandescent bulb 11, whose front part is constructed directly, in known manner, as a converging lens 12, in which case the object distance, i.e. the distance between the filament 11a shown in FIG. 2 and the collecting lens 12 is less than the focal length of the lens 12, so that this lens 12 produces an emerging divergent beam of rays. The incandescent bulb 11 is arranged in the lamp holder 10 so that its filament 11a is arranged at least approximately parallel to the pivot axis of the lid 3 with the mirror 4. Furthermore, the lamp holder 10 is inclined with respect to the lower and upper walls of the casing (FIG. 3) so that the incandescent bulb 11 and thus the beam of rays emitted is directed obliquely upwards, if the user holds the casing horizontally in front of his mouth. Observation in the unfolded mirror is thus made easier.

The lamp holder 10 is attached to the inner wall of the insert 7 and can therefore be removed from the casing 1 together with this insert 7. Attached between lateral projections on the inner wall of the insert is the securing plate 13 of a locking part 14 (FIG. 1), which is connected to the securing plate 13 by a flexible area 15 having a smaller wall thickness and at this point is bent at right-angles to the securing plate 13. Formed on the upper side of the locking part 14 are knurling 16 accessible after opening the lid 3 and a projection 17 serving as a hook, which in the inserted position of the insert 7 illustrated in FIG. 1 locks the latter against an edge 18 of the casing 1. In order to remove the insert 7, it is solely necessary to bend the locking part 14 elastically inwards, by means of slight pressure on the knurling 16, to such an extent that the projection 17 can slide below the edge 18 of the casing.

Figure 3:
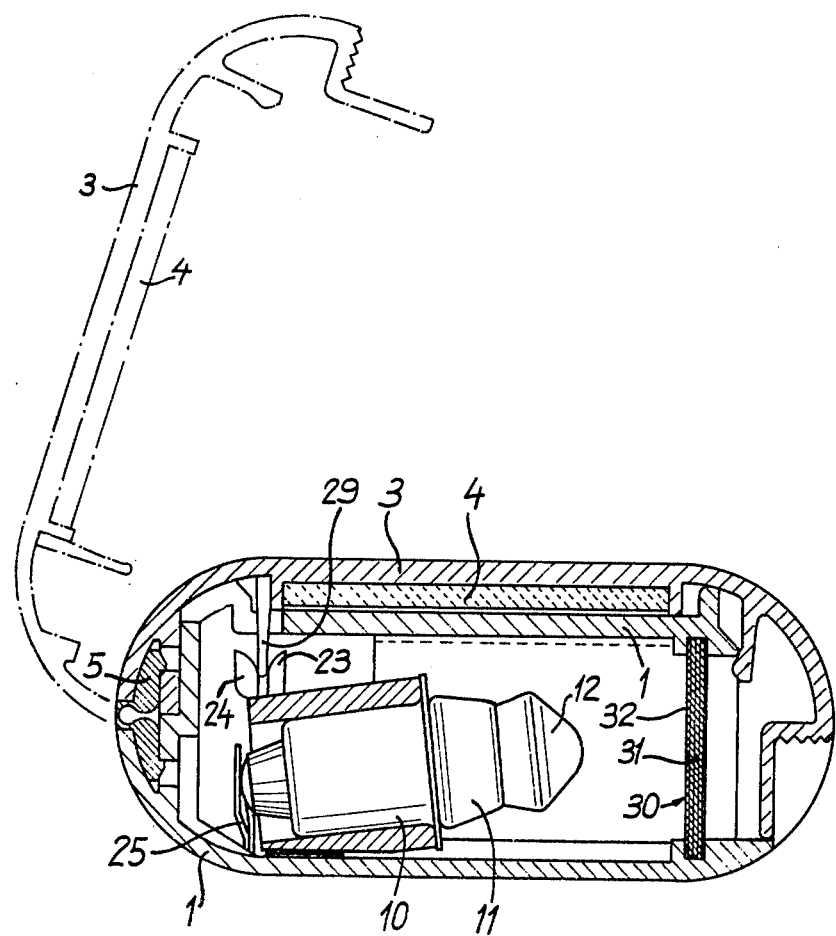
FIG. 3 is a sectional view on line III—III of FIG. 2, the closed lid being shown in full line and the open lid being shown in dot-dash lines

In the example in question, the insert 7 supports three batteries 6 (FIG. 2), which are connected electrically in series and retained in known manner by way of electrical leads 19 with resilient tongues 20. The left-hand pole of the lower battery 6 in FIG. 2 is in contact with one side of a curved metal contact spring 21 approximately of S-shape, the other side of which inside the lamp holder 10 forms one connection contact for the incandescent bulb 11. The first-mentioned, namely the right-hand side of this contact spring 21 according to FIG. 2 is located between two parallel wall portions of the insert 7, which form the inner wall of the insert 7 constructed as a double wall. The right-hand pole of the upper battery 6 according to FIG. 2 is in contact with a contact strip 22, which consists essentially of a strip extending along the upper battery and of a section bent at right-angles at its inner end, in the direction of the lid 3, the free end of which section forms a spherically curved spring contact 23 (FIG. 3). Located opposite this spring contact 23 in the form of a mirror image is a likewise spherically curved spring contact 24 (FIG. 3), which is formed at one end of a further bent contact strip 25, whose other end forms the other connection contact for the rear end of the incandescent bulb 10 (FIG. 2). Both contact strips 22 and 25 are attached with the interposition of an insulating member 26 to a projection 27 of the insert 7 by means of a bolt 28 of insulating material, which passes through corresponding openings in the two contact strips 22 and 25. The two spherically curved spring contacts 23 and 24 are arranged such that when the lid 3 is closed, as illustrated in full line in FIG. 3, they are spread apart by a wedge-shaped flat projection 29 formed on the lid, so that the circuit of the incandescent bulb 11 is interrupted. On the other hand, when the lid 3 is opened, the flat projection 29 is removed from between the two spring contacts 23 and 24, as shown in dot-dash line in FIG. 3, so that on account of their elasticity, these two spring contacts are able to come into contact and thus close the circuit for the incandescent bulb 11.

A filter device 30 is inserted in the casing 1 in front of the incandescent bulb 11. This filter device includes a rectangular blue colored glass 31, which is preferably colored throughout and of a dichroic filter 32 formed by layers applied to the inner side of this colored glass 31. When using fluorescein, this dichroic filter 32 has a transmission characteristic as illustrated diagrammatically in FIG. 4. The wave lengths are plotted in nm on the X-axis of the diagram and the transmission is plotted as a percentage on the Y-axis. The curve drawn in full line relates to a beam of rays arriving at right-angles to the plane of the filter, the curve drawn in broken lines relates to beams of light which arrive at an angle of approximately 45°. It can be seen that this filter allows light to pass in the range of short wave lengths of up to 500 nm and then the transmission drops suddenly and steeply with increasing wave length, in which case for a wave length of approximately 505 nm, the transmission or absorption is approximately 50% and for only slightly greater wave lengths of approximately 510 to 520 nm, the transmission amounts to less than 10%. This transmission or absorption curve is adapted to a fluorescein solution, which is stimulated essentially by rays with wave lengths of 495 nm and whose emitted radiation essentially has wave lengths of 525 nm. In this way, the range of fluorescent radiation to be observed is filtered out of the incandescent bulb light, in order to obtain an easily visible contrast. As is also shown by the curve according to FIG. 4, the dichroic filter blocks out perpendicularly incident rays up to wave lengths of approximately more than 700 nm, i.e. into the long wave visible red range and then in the infrared range once again allows light to pass. This transmission in the infrared range has no function, insofar that only the visible red is filtered out in a satisfactory manner, the presence of which would cover any fluorescent radiation.

Figure 4:
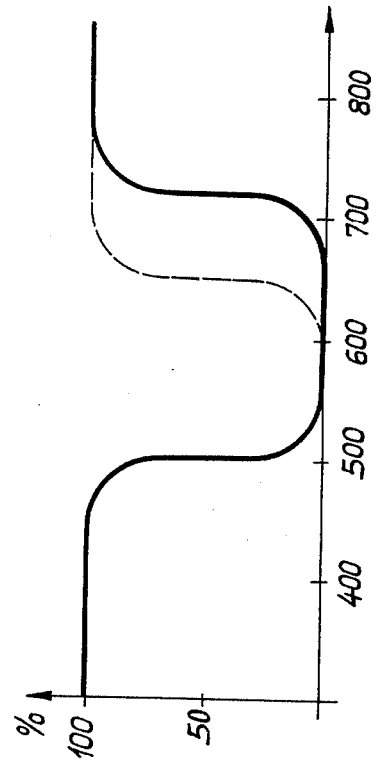
FIG. 4 shows the transmission characteristics of a dichroic filter.

However, since one uses a divergent beam of rays according to the invention, the rays strike the dichroic filter at a greater angle of incidence the further they are from the optical axis. The transmission or absorption properties of this filter thus alter accordingly, which filter, according to the interrupted curve of FIG. 4 is highly transmissive for rays with an angle of incidence of approximately 45° with wave lengths of 650 nm, i.e. in the visible red range. This has the result that the illuminated area to be inspected appears red in the vicinity of the edge, which prevents a resonable diagnosis. In order to prevent this effect in a simple manner, which effect is caused by the use of a divergent beam of rays and of a dichroic filter, the filter device 30 comprises an additional blue filter 31, which absorbs the visible red light allowed through by the dichroic filter with a greater or lesser angle of incidence.

Furthermore, the additional blue filter has the advantage that parts of teeth or the teeth not covered with a fluorescent solution appear blue and therefore contrast particularly well with respect to the fluorescent light, which appears yellow or yellowish/green.

In conjunction with the filament 11a of the incandescent bulb 11, which filament is directed horizontally when the casing 1 is held horizontally, the afore-mentioned lens 12 provides a divergent beam of rays with a substantially oval cross section, the arrangement being such that the illuminated oval region corresponds at least approximately to the size of the open mouth, when the diagnostic lamp is held at a distance of 8 to 12 centimeters, preferably approximately 10 centimeters from the mouth. In order to eliminate any stray light and in particular to prevent the user from being dazzled, the plate forming the filter device 30, as afore-mentioned, is rectangular, the long rectangular side being parallel to the pivot axis of the lid 3. In this way, the filter device 30 forms a corresponding rectangular aperture which limits the size of the beam of rays emitted. In order to achieve adequate brightness, on the one hand a reflector 34 in the form of a concave mirror is preferably provided behind the front area of the incandescent bulb 11, as shown in FIG. 2 and on the other hand, the incandescent bulb 11 is preferably supplied with an excess voltage of 20 to 30% for example. In the example in question, three 1½ volt batteries are provided, thus giving a voltage of 4.5 volts, by which an incandescent bulb 11 with a rated voltage of only 3.7 volts is operated.

The complete illumination of all the teeth and gums as well as the convenient observation is further facilitated due to the fact that the lid 3 with the mirror 4 is adjustable, i.e. can be folded back into any position, where it is held by friction and also that as afore-mentioned, the incandescent bulb 11 is arranged somewhat obliquely in the casing 1 (FIG. 3). In this way, each user is able to adapt the diagnostic lamp as regards the direction of illumination and the direction of observation, to his own particular morphology.

On its upper side, the insert 8 for the dispenser 9 likewise has a locking part with knurling 35 (FIG. 1) and a hook-like projection 36, which in the inserted state locks the insert 8 against one edge 37 of the casing 1. The insert 8 can be easily unlocked and then easily removed from the casing 1 by pressing on the knurling 35 which is accessible when the lid 3 is opened.

The dispenser 9 is an approximately square container consisting of a resilient flexible synthetic material and comprises an outlet connection 38, to which is screwed a bush 39 with a hinged outlet pipe 40. In the folded inoperative position of this outlet pipe 40 illustrated in FIG. 2, in which it fits in a recess on the end face of the insert 8, the inner opening 41 of the bush 39 and thus the outlet connection 38 are closed-off by the side wall of the end of the outlet pipe 40 adjacent the pivot. In order to use the dispenser 9, the outlet pipe 40 is swung out about its pivot point 42 in counterclockwise direction according to FIG. 2, so that now the inner channel 60 of the outlet pipe 40 opening into the outlet opening 43 is in alignment with the inner opening 41 of the bush 39 and the outlet connection 38. Now in order to eject the liquid from the dispenser 9 through the outlet pipe 40, the user needs to press solely on the protruding area 9a of the dispenser 9, which area is provided in the lower wall of the dispenser and is accessible through a corresponding opening 44 on the underside of the casing 1 (FIG. 1). After this, the outlet pipe 40 is swung back into its folded inoperative position, in which it closes-off the dispenser 9.

In order to carry out an inspection of the teeth, it is solely necessary to open the lid 3, which in the closed position covers the filter device 30 and thus protects the latter (FIG. 3), due to which opening operation, as afore-described, the incandescent bulb 11 is switched-on.

The afore-described diagnostic lamp, which in the drawings is illustrated with a scale of approximately 2:1, is in the form of a portable pocket appliance with a length of approximately 110 mm, a width of approximately 55 mm and a thickness of approximately 22 mm. The filter device 30 limiting the emergent beam of rays has dimensions of approximately 18 mm × 14 mm. With a supply voltage of approximately 4.5 volts, the incandescent bulb 11 consumes only approximately 2.4 watts.

The invention is not limited to the embodiment described, but may have many variations as regards the construction of the casing, the electrical parts, the dispenser and the optical system. Thus, in particular, the filter device may consist of two separate filters, namely a blue colored filter and a dichroic filter.

What is claimed is:

1. A portable diagnostic lamp for fluorescent excitation of a fluorescible material applied to the teeth, which fluorescible material is stimulated essentially by blue light, the lamp comprising: a casing; a small battery-powered incandescent bulb; a filter device adapted to the fluorescent substance and comprising a dichroic filter and a blue color filter whereby the device transmits at least a substantial portion of the spectral range of the incandescent bulb necessary for stimulating the fluorescible material and absorbs at least a substantial portion of the spectral range of the fluorescent light, said filter device defining a rectangular outlet window; a mirror attached to the casing and foldable along a pivot axis, which mirror enables a user to observe the illuminated teeth, the longer sides of the outlet window being parallel to the pivot axis of the mirror; a filament within said incandescent bulb, said filament being arranged at least approximately parallel to the pivot axis of the mirror; and a lens which is located in the path of rays emitted by the incandescent bulb and which provides a diverging emergent beam of rays.

2. A diagnostic lamp as claimed in claim 1, in which, in use, the incandescent bulb is arranged with its axis inclined towards the upper side of the casing and with its front end pointing obliquely upwards.

3. A diagnostic lamp as claimed in claim 1, in which the filter device includes a blue colored glass and layers deposited thereon, forming the dichroic filter.

4. A diagnostic lamp as claimed in claim 1, in which a concave reflector is provided on the incandescent bulb.

5. A diagnostic lamp as claimed in claim 1, in which the mirror is adjustably mounted on the casing and is constructed as a concave mirror.

6. A diagnostic lamp as claimed in claim 1, in which the incandescent bulb and the lens are constructed in one-piece.

7. A diagnostic lamp as claimed in claim 1, in which the incandescent bulb can be operated with an excess voltage which is between 20 and 30% above its rated voltage.

8. A diagnostic lamp as claimed in claim 1, in which the incandescent bulb is a miniature or dwarf incandescent bulb.

9. A diagnostic lamp as claimed in claim 1 wherein said lens is arranged so that the divergence of rays is such that at a distance of 8 to 12 centimeters from the incandescent bulb, an area corresponding to the oval defined by the open mouth is illuminated.

* * * * *